United States Patent
Del Soldato

(10) Patent No.: US 6,573,252 B1
(45) Date of Patent: Jun. 3, 2003

(54) MEDICINE NITRATE SALTS

(75) Inventor: Piero Del Soldato, Milan (IT)

(73) Assignee: Nicox, S.A., Paris (FR)

( * ) Notice: Subject to any disclaimer, the term of this patent is extended or adjusted under 35 U.S.C. 154(b) by 0 days.

(21) Appl. No.: 09/743,801

(22) PCT Filed: Jul. 20, 1999

(86) PCT No.: PCT/EP99/05170

§ 371 (c)(1),
(2), (4) Date: Jan. 19, 2001

(87) PCT Pub. No.: WO00/06585

PCT Pub. Date: Feb. 10, 2000

(30) Foreign Application Priority Data

Jul. 28, 1998 (IT) .................................... MI98A1744

(51) Int. Cl.$^7$ ..................... C07F 9/38; A61K 31/662; A61K 31/663; A61P 19/08
(52) U.S. Cl. ..................... 514/108; 562/13; 562/453; 562/456; 562/457; 514/567
(58) Field of Search .................. 562/13, 456, 457, 562/453; 514/102, 567

(56) References Cited

FOREIGN PATENT DOCUMENTS

| EP | 0 012 866 A1 | 7/1980 |
|---|---|---|
| EP | 0 252 502 A2 | 1/1988 |
| EP | 0 325 482 A1 | 7/1989 |
| EP | 0 522 576 A2 | 1/1993 |
| EP | 0 531 253 A1 | 3/1993 |
| EP | 0 546 548 A1 | 6/1993 |
| EP | 0 561 296 A1 | 9/1993 |
| JP | 92356496 | 12/1992 |
| JP | 93032684 | 2/1993 |
| JP | 93222073 | 8/1993 |
| WO | WO93/00348 | 1/1993 |
| WO | WO 93/12122 | 6/1993 |
| WO | WO 94/27980 | 12/1994 |
| WO | WO 95/15315 | 6/1995 |
| WO | WO 95/30641 | 11/1995 |

OTHER PUBLICATIONS

New Guide to Medicine & Drugs, "Muscles, Bones, and Joints", Brit. Med. Association 1997, p. 115.

Martindale, The Extra Pharmacopeia, "Analgesics Anti–inflammatory Agents and Antipyretics", vol. 31, 1996, pp 11–13.

Bradley et al, The Journal of Investigative Dermatology, "Measurement of Cutaneous Inflammation: Estimation of Neutrophil Content with an Enzyme Marker", vol. 78, 1982, pp 206–209.

Primary Examiner—Richard L. Raymond
Assistant Examiner—Kahsay Habte
(74) Attorney, Agent, or Firm—Arent Fox Kintner Plotkin & Kahn

(57) ABSTRACT

The present invention relates to nitrate salts of compounds having therapeutic activity in bony disorders, such compounds being characterized in that they contain at least a reactive group capable of being salified with nitric acid.

17 Claims, No Drawings

MEDICINE NITRATE SALTS

The present invention relates to compositions to be used in the therapy and prevention of bony disorders, such as those of the bony tissue and articulations. More specifically it relates to compositions having an improved therapeutic activity and improved gastrointestinal tolerability.

It is known in the art that the pharmacologic treatment of bony disorders implies therapies directed to control pathophysiologic processes such as those concerning the bony tissue and articulations.

Among the compounds known in the art for the pharmacologic treatment of the muscle skeletal and articular system disorders the following ones can be mentioned (see "New Guide to Medicine & Drugs", Brit. Med. Association 1997, pag. 115; "Martindale, The Extra Pharmacopeia" vol. 31, 1996 pages 11–13):

diphosphonates (Alendronate, Pamidronate, Risedronate, etc.);

"oxicams", i.e. Piroxicam, Tenoxicam; Aminopyrine; Tomoxiprol; Penicillamine; Methotrexate; etc.

They are medicines having a limited efficacy and having the inconvenience of causing lesions of the gastrointestinal duct, in particular of the stomach. Diphosphonates cause also lesions in the esophagus.

Other compounds used in the bony disorder therapy are anti-leukotriene medicines, for intance Ibudilast, Pranlukast, etc.; aminosalicylates. The efficacy and the gastrointestinal tolerability of these medicines is not optimal.

Compounds suitable to overcome the drawbacks shown by the medicines used in the bony disorder treatment have not yet been available in the art.

The need was felt to have available compounds for use in the bony disorder treatment with improved therapeutic features and tolerability and/or having an higher efficay.

The Applicant has unexpectedly and surprisingly found compounds and their compositions having improved pharmacotherapeutic properties.

It is an object of the present invention nitrate salts of compounds having a therapeutic activity in bony disorders, or their pharmaceutical compositions, said compounds being characterized in that they contain at least a reactive group capable to be salified with nitric acid, said compounds being selected from the following classes:

Class. F1):

-continued
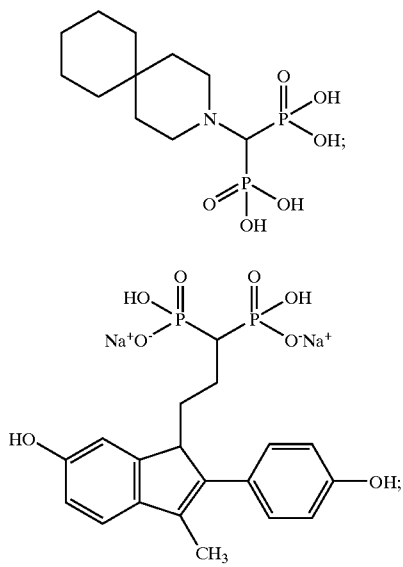
(F1m)
(F1n)
(F1o)
(F1p)
Class F2A:
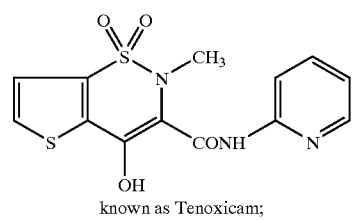
known as Tenoxicam;
(F2AI)
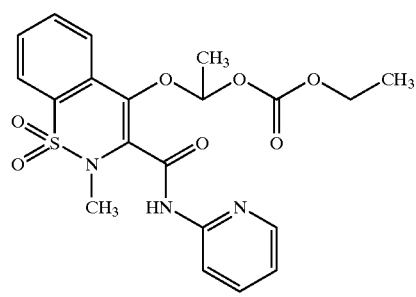
known as Ampiroxicam;
(F2AII)
-continued
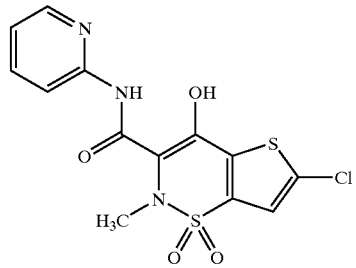
known as Lornoxicam;
(F2AIII)
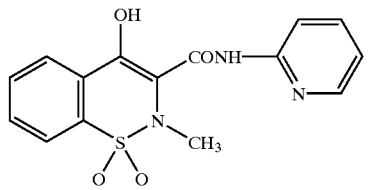
known as Piroxicam;
(F2AIV)
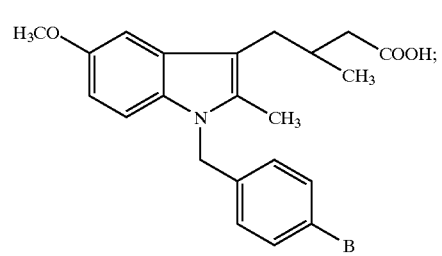
(F2AV)
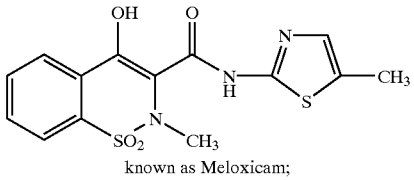
known as Meloxicam;
(F2AVI)
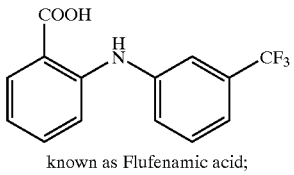
known as Flufenamic acid;
(F2AVII)
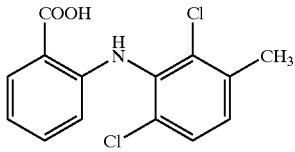
known as Meclofenamic acid;
(F2AVIII)
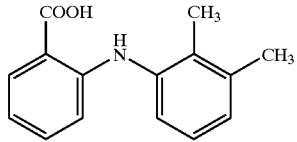
known as Mefenamic acid;
(F2AIX)

(F2AX) known as Niflumic acid;

(F2AXI) known as Aceclofenac;

(F2AXII) known as Diclofenac (sodium salt);

(F2AXIII) known as Etodolac;

(F2AXIV) known as Mesalamine (F2AXV) known as Methotrexate;

(F2AXVI) known as Penicillamine;

(F2AXVIII) known as Tramadol;

Class F2B:

(F2BI) known as Tomoxoprol;

(F2BII) known as Droxicam;

(F2BIII) known as Celecoxib;

(F2BIV)

(F2BV)

-continued (F2BVI)

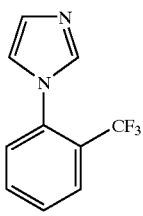

Class F3:

(F3a)

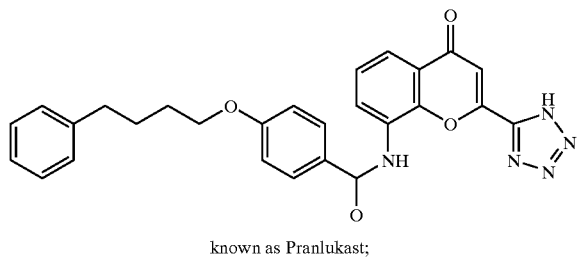

known as Pranlukast;

(F3b)

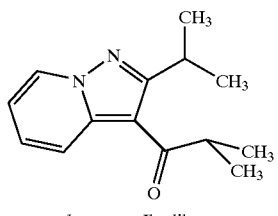

known as Ibudilast;

(F3c)

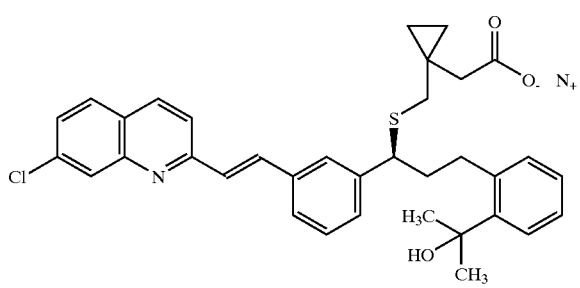

known as sodic salt Montelucast.

The nitrate salts of the present invention can be obtained also by using the above mentioned compounds of the described classes, which optionally contain one or more —ONO$_2$ groups covalently bound to the molecule by one of the following bivalent linking bridges YO wherein Y is a $C_1$–$C_{20}$ alkylene linear or branched when possible, preferably from 2 to 5 carbon atoms, or an optionally substituted cycloalkylene from 5 to 7 carbon atoms;

$Y_1$ selected from:

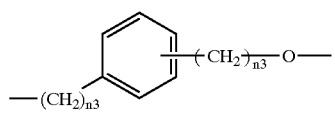

wherein $n_3$ is an integer from 0 to 3;

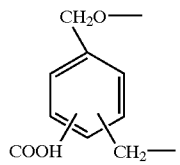

wherein nf' is an integer from 1 to 6 preferably from 2 to 4;

$$-(CH_2-CH_2-O)_{nf'}- \atop R_{1f}$$

wherein $R_{1f}$=H, $CH_3$ and nf is an integer from 1 to 6; preferably from 2 to 4.

Said compounds containing a —ONO$_2$ group covalently bound to the molecule through one or more of said bivalent linking bridges, or spacers, are prepared as described in the European patent application 759,899 in the name of the Applicant, herein incorporated by reference.

Preferably these compounds containaing —ONO$_2$groups covalently bound to the molecule by said spacers are selected from the compounds of class F2A (in the Ampiroxicam (F2AII) case by previously hydrolising the ethyl ester) and Montelukast of class F3.

It has been found by the Applicant that the nitrate salts of compounds containing at least a nitrate group covalently bound to the molecule by one or more of the above spacers, show an higher pharmacological activity. For instance the nitrate salt of the 5-aminosalicylic acid derivative (mesalamine) containing a nitrate group covalently bound to the molecule by a butyl spacer, has resulted more active than the unsalified compound in the pharmacological model indicated in the examples.

The precursors to obtain the salts of the present invention are preferably selected from the following:

class F1: Alendronate;
class F2A: Piroxicam, Diclofenac, Etodolac, Flufenamic acid;
class F2B: Tomoxiprole;
class F3: Pranlukast.

In the compositions according to the present invention also the isomers, when they are available, of the compounds belonging to the above described classes, can be used.

Examples of isomers are cis-, trans-, optical isomers D and L or the racemic, enantiomer. In general one isomeric form has higher activity with respect to the other, e.g. D form with respect to L form or viceversa.

The compound salts belonging to above classes contain at least one nitrate ion mole/compound mole. Preferably the ratio between the nitrate ion moles and the precursor moles is unitary. Salts with higher molar ratio are obtained when in the molecule other aminic groups basic enough to be salified, are present.

The salts of the present invention are formulated in the corresponding pharmaceutical compositions according to well known techniques in the field, together with the usual excipients; see for instance the "Remington's Pharmaceutical Sciences 15a Ed." volume.

The invention salt dosages in their pharmaceutical compositions are the same, and generally lower than those of their precursors of the mentioned classes. However since they are generally more tolerated, it is possible to use them also in dose higher than those of the precursors without having the side effects appearing with the precursors at high doses.

The precursors of the salts belonging to the above mentioned classes are prepared according to the methods described in the following references:

Class F1:
disodic Alendronate, disodic Pamidronate, sodic Risedronate: see the "Index Merck $14^a$ Ed." volume, herein incorporated by reference; disodic Ibandronate EP 252,502, formula (F1e) compound EP 325,482, formula (F1f) compound: EP 531,253, formula (F1g) compound: EP 592,488, formula (F1h) compound: EP 522,576, formula (P1i) compound: EP 546,548, formula (F1l) compound: EP 561,296, formula (F1m) compound: JP 93032684 (C.A. ref. Vol.119 226194d), formula (F1n) compound: JP 93222073 (C.A. ref. Vol.120 134926m), formula (F1o) compound: JP 92356496 (C.A. ref. Vol.119 095828p), formula (F1p) compound: WO 93/12122;

Class F2A:
Tenoxicam, Ampiroxicam, Lornoxicam, Piroxicam, Meloxicam, Flufenamic acid, Meclofenamic acid, Mefenamic acid, Niflumic acid, Aceclofenac, Diclofenac, Etodolac, Mesalamine, Methotrexate, Penicillamine, Tramadol: see "Index Merck volume, $14^a$ Ed.", herein incorporated by reference;

Class F2B:
Tomoxiprole: EP 12,866; Droxicam: "Index Merck $14^a$ Ed."; Celecoxib: WO 94/2,798, formula (F2BIV) compound WO 95/15,315; the compounds of formula F2BV (7-nitro indazol) and F2BVI (1,2-(trifluoromethylphenyl)imydazol) are commercialized by Lancaster Synthesis, Morecam—England.

Class F3:
Sodic salt Pranlukast, Ibudilast, Montelukast: see the "Index Merck volume, $14^a$ Ed.".

The salts of the present invention are obtainable according to one of the following methods.

If the substance to be salified is available as free base or as a corresponding salt soluble in an organic solvent, which preferably does not contain hydroxyl groups, for example acetonitrile, ethyl acetate, tetrahydrofuran, etc., the salt is prepared by dissolving the substance in the solvent at a concentration preferably equal or higher than 10% w/v, adding the amount of concentrated nitric acid corresponding to the moles of salifiable minic groups present in the compound. The nitric acid is preferably diluted in the same solvent. Preferably during and after the addition the mixture is cooled at temperatures between 20° C. and 0° C. The product is generally recovered by filtration and washed with the solvent.

When on the contrary the substance is not very soluble, or it is available as a not very soluble salt in the above mentioned solvents, the corresponding mixtures with hydroxylated solvents can be used. Examples of such solvents are methyl alcohol, ethyl alcohol and water. Precipitation can be quickened by diluting the so obtained mixture, after the addition of nitric acid, with an apolar solvent.

When the starting product is salified with hydrochloric acid, it is possible to prepare the salt with nitric acid directly adding silver nitrate to the compound solution. After filtering silver chloride, the solution is concentrated and cooled to recover the nitrate salt.

When the starting product is a salt, it is also possible to free the corresponding base by a treatment with a sodium or potassium bicarbonate or carbonate saturated solution, or with a sodium or potassiumn hydroxide diluted solution. The base is then extracted by a suitable organic solvent (for example halogenated solvents, esters, ethers), which is then dried. The organic solution is evaporated and then one proceeds according to the preceding preparation methods, by dissolving the base in acetonitrile or in the other above mentioned solvents.

The following examples are given with the purpose to illustrate the invention and they are not limitative of the same.

EXAMPLE 1

Piroxicam Nitrate Salt Preparation

A Piroxicam solution (3 g, 9.05 mmoles) in acetonitrile (30 ml) and tetrahydrofuran (50 ml) is treated at +4° C. with nitric acid at 65% (0.63 ml) dissolved in acetonitrile (5 ml). The mixture is stirred and then let stay. After 30 minutes at +4° C., it is filtered and a precipitate is collected, which is washed with ethyl ether and dried under vacuum.

A white solid (3.23 g) having melting point 120°–123° C. is obtained.

Elemental analysis:

| calc (%)  | C 45.68 | H 3.58 | N 14.12 | S 8.13 |
| --- | --- | --- | --- | --- |
| exper. (%) | C 45.76 | H 3.54 | N 14.11 | S 8.16 |

EXAMPLE 2

Alendronate Nitrate Salt Preparation

An Alendronate solution (0.92 g, 3.7 mmoles) in 50% nitric acid (2 ml) is dropped at the temperature of +4° C. in ethyl ether (30 ml). The mixture is stirred and then let stay. After 40 minutes at +4° C., the precipitate is filtered, washed with ethyl ether and dried under vacuum. A white amorphous solid is obtained.

Elemental analysis:

| calc (%)  | C 15.39 | H 4.52 | N 9.01 |
| --- | --- | --- | --- |
| exper. (%) | C 15.41 | H 4.50 | N 8.99 |

EXAMPLE 3

Penicillamine Nitrate Salt Preparation

A (L)-Penicillamine (5 g, 33.5 mmoles) in methanol (50 ml) is treated at +4° C. with nitric acid 65% (2.5 ml) dissolved in acetonitrile (7 ml). The mixture is stirred and let stay. After 15 minutes at +4° C. ethyl ether is added, the precipitate is filtered and dried under vacuum. An amorphous solid is obtained (3.2 g).

Elemental analysis:

| calc (%) | C 28.30 | H 5.65 | N 13.19 | S 15.11 |
|---|---|---|---|---|
| exper. (%) | C 28.29 | H 5.66 | N 13.22 | S 15.08 |

EXAMPLE 4

Methotrexate Nitrate Salt Preparation

A Methotrexate solution (5 g, 11.00 mmoles) in methanol (60 ml) is treated at +4° C., under stirring, with nitric acid 65% (0.82 ml) dissolved in acetonitrile (5 ml).

After 30 minutes at +4° C. the solution is treated with ethyl ether. The precipitate is filtered and washed with ethyl ether. It is dried under vacuum. An amorphous solid (2.2 g) is obtained.

Elemental analysis:

| calc (%) | C 46.42 | H 4.44 | N 24.35 |
|---|---|---|---|
| exper. (%) | C 46.44 | H 4.40 | N 24.39 |

EXAMPLE 5

Tomoxiprole Nitrate Salt Preparation

A Tomoxiprole solution (2 g, 6.32 mmoles) in acetonitrile (50 ml) and methanol (18 ml) is treated at +4° C. with nitric acid at 65% (0.432 ml) dissolved in acetonitrile (10 ml). The mixture is stirred and then let stay at +4° C. After 30 minutes the solution is treated with ethyl ether.

The formed precipitate is filtered, washed with ethyl ether and dried under vacuum. A white solid m.p. 197°–199° C. is obtained.

Elemental analysis:

| calc (%) | C 65.81 | H 5.52 | N 11.01 |
|---|---|---|---|
| exper. (%) | C 65.78 | H 5.59 | N 11.02 |

EXAMPLE 6

Preparation of the 5-Amino-2-hydroxybenzoic Acid (4-nitroxy)-butyl Ester (5-ASA-NO$_2$)

EXAMPLE 6a

Preparation of the 5-tert-Butoxycarbonylamino-2-hydroxybenzoic Acid

To a suspension of 5-amino-2-hydroxybenzoic acid (15 g, 98 mmoles) in dioxane (105 ml) and water (150 ml) triethylamine (24.6 ml, 176 mmoles) is added. To the obtained solution di-tert-butyl-dicarbonate (25.65 g, 118 mmoles) is added. The reaction mixture is left under stirring at room temperature for 4 days. Finally the solution is concentrated under vacuum up to a volume of a about 150 ml, cooled by ice and acidified with hydrochloric acid at 5%, extracting then with ethyl acetate. The organic phase is recovered and washed with water. The organic phase is anhydrified by sodium sulphate. By evaporating the solvent under vacuum the product is recovered as amorphous solid (20.8 g).

EXAMPLE 6b

Preparation of the 5-tert-Butyloxy-carbonylamino-2-hydroxy-benzoic-(4-bromo-butyl) Ester Acid To a solution of 5-tertbutyloxy-carbonylamino-2-hydroxy-benzoic acid (20 g, 85.7 mmoles) in tetrahydrofuran (200 ml) triphenylphosphine (44.9 g, 171 mmoles) and lastly carbon tetrabromide (56.7 g, 171 mmoles) are added. The reaction mixture is left under stirring at room temperature for 24 hours and then evaporated under vacuum. The obtained residue is purified by silica gel column chromatography (eluent: n.-hexane/ethyl acetate 8/2 vol./vol.), monitoring the content of the collected fractions by chromatography on thin layer. The product is obtained by collecting the head fractions, after elution from the column of the CBr$_4$ reactive used in the synthesis. The fractions are collected and dried. A white solid (21.16 mg) having m.p. 108°–111° C. is recovered.

EXAMPLE 6c

Preparation of the 5-tertbutyloxy-Carbonylamino-2-hydroxy-benzoic-(4-nitroxy-butyl) Ester Acid A solution of 5-tertbutyloxy-carbonylamino-2-hydroxy-benzoic acid-(4-bromo-butyl) ester (21.16 g, 57.6 mmoles) in acetonitrile (150 ml) is heated at 80° C., in the dark, for 5 hours. After cooling at room temperature the solid is filtered and the solvent is recovered, which is evaporated to dryness obtaining a residue which is purified by silica gel column chromatography by using as eluent n.hexane/ethyl acetate 7/3 vol./vol.), monitoring the content of the collected fractions by chromatography on thin layer. The head fractions containing the compound are evaporated to dryness obtaining 12.6 g of a white solid having m.p. 107°–109 C.

EXAMPLE 7 (comparative)

Preparation of the Hydrochloride Salt of the 5-Aminosalicylic Acid (4-nitroxy)-butyl Ester (5-ASA-NO$_2$.HCl)

A solution of the 5-tert-butyloxy-carbonylamino-2-hydroxy-benzoic acid-(4-nitroxy-butyl) ester (10 g, 28.6 mmoles) is dissolved in ethyl acetate (8 ml) and cooled at 0° C. Ethyl acetate/HCl 3 M (30 ml), prepared by bubbling gaseous HCl in ethyl acetate is added under stirring until the required HCl molar concentration is obtained. The mixture is allowed to reach the room temperature and is left under stirring for 2 hours. A solid is formed, which is filtered, washed with ethyl ether and dried under vacuum. The product (7.1 g) is obtained as a white solid having m.p. 136°–140° C.

Elemental analysis:

| calc (%) | C 43.09 | H 4.89 | N 9.13 | Cl 11.56 |
|---|---|---|---|---|
| exper. (%) | C 43.05 | H 4.88 | N 9.10 | Cl 11.54 |

EXAMPLE 8

Preparation of the Nitrate Salt of the 5-amino-2-hydroxybenzoic Acid (4-nitroxy)butyl Ester (5-ASA-NO$_2$.HNO$_3$)

To a solution of the hydrocloride salt of the 5-aminosalicylic acid 4-nitroxybutyl ester (2 g, 7 mmoles) in a mixture of acetonitrile (50 ml) and tetrahydrofuran (15 ml) nitrate silver (1.19 g, 7 mmoles) is added. After 10 minutes the formed salt (AgCl) is filtered. The solution is let stay at room temperature for 30 minutes, then the precipitate is filtered, washed with ethyl ether and dried under vacuum. The salt (1.27 g) is obtained as a whitish solid having m.p. 123°–128° C.

Elemental analysis:

| calc (%) | C 39.66 | H 4.50 | N 12.61 |
|---|---|---|---|
| exper. (%) | C 39.70 | H 4.53 | N 12.67 |

PHARMACOLOGICAL TESTS

EXAMPLE 9

Acute Toxicity

To a group of 10 rats weighing 20 g a single dose equal to 100 mg/kg of Piroxicam nitrate salt (Example 1), has been administered by cannula orally in a carboxymethylcellulose aqueous suspension 2% w/v.

The animals are kept under obsevation for 14 days. In no one of the animals of the group the toxic symptom presence was noticed.

EXAMPLE 10

Gastric Toxicity of Piroxicam Nitrate Salt (Ex. 1) Compared with Piroxicam

To 3 groups of 10 rats each, kept on empty stomach since 24 hours, orally are administered:

5 ml/Kg of carboxymethylcellulose aqueous suspension 2%.

an amount of nitrate Piroxicam corresponding to 100 mg/kg of Piroxicam in 5 ml/kg of carboxymethylcellulose aqueous suspension 2%.

an amount of hydrocloride Piroxicam corresponding to 100 mg/kg of Piroxicam in 5 ml/kg of carboxymethylcellulose aqueous suspension 2%.

Six hours later the animals are sacrificed and the gastric lesion incidence is evaluated. The results are reported in Table 1 and they show that the rats treated with Piroxicam nitrate show an improved gastric tolerability compared with Piroxicam hydrochloride.

EXAMPLE 11

Myeloperoxydase Activity of the 5-Aminosalicylic Acid (4-nitroxy)butyl Ester Compared with that of the Corresponding Hydrochloride and Nitrate Salts, in an Acute Colitis Model 4 groups of 6 animals each have been formed. The groups were treated, respectively, with the carrier (carboxymethylcellulose aqueous solution 1%), 100 mg/Kg of 5-ASA, a 5-ASA-NO$_2$.HCl amount corresponding to 100 mg/kg of 5-ASA, an amount of 5-ASA-NO$_2$.HNO$_3$ correspsonding to 100 mg/kg of 5-ASA.

The animals were treated by rectal route with the above compounds at zero time. After one hour the animals were treated with 0.5 ml of a 60 mg/ml solution of 2,4,6,trinitrobenzensulphonic acid in ethyl alcohol 50%. After two hours the animals were treated again by rectal route with the same compounds and at 12 hour intervals up to a total of 6 administrations.

The tissular levels of the myeloperoxydase (MPO) enzym have been measured which is an inflammatory process marker in various tissues, among which the bony-articular one (C. Rathakrishnan et Al., "Release of oxygen radicals by articular chondrocytes: A study of luminol-dependent chemiluminescence and hydrogen peroxide secretion" J. Bone Miner. Res. 7/10 1139–1148 1992).

The myeloperoxydase activity was measured by using a modified version of the experimental model described by Bradley et al. J. Invest. Dermatol. 78, 206–209, 1982. Samples of intestinal tissue were drawn from each animal, which were suspended in 0.1% of hexadecyltrimethylammonium bromide (50 mg/ml) at a pH 6 and homogenized for 15 seconds (Polytron® PT-7 generator). The samples were frozen and then defrosted three times subsequently before being centrifuged (9,000 g) for 2 minutes in an Eppendorf® Benchtop centrifuge. The myeloperoxydase activity was measured by adding 7 µl of the surnatant to 200 µl of o-dianisidine (Sigma) reactant and measuring the optical density variation at 450 nm in a two minute time in a Microtitre Multiscan®. The reactant contained 0.0005% of hydrogen peroxide as substratum for the myeloperoxydase enzym. One unity of the myeloperoxydase activity was defined as the one capable to convert an hydrogen proxide micromole to water in one minute at 22° C. The results are reported in Table II and are expressed as unit number of the myeloperoxydase activity/tissue mg (wet).

From the table it is noticed that in the group treated with 5-ASA-NO$_2$.HNO$_3$ the myeloperoxydase activity is lower than that of the other groups.

EXAMPLE 12

Prevention of the Gastric Damage Induced by Aspirin by Administering Alendronate in Comparison with Alendronate Nitrate Salt Three groups of 5 rats each were treated by oral route with gastric probe as indicated hereinafter:

I group: treated with Alendronate (Alen.) at the dose of 80 mg/Kg.

II group: 1 h before the Alendronate 80 mg/Kg dose, ASpirin (Asp.) was supplied per os at the dose of 125 mg/Kg.

III group: 1 h before the Alendronate nitrate, (Alen.HNO$_3$) corresponding to the Alendronate 80 mg/Kg dose, Aspirin was supplied per os at the dose of 125 mg/Kg.

The evaluation of the gastric damage was carried out sacrificing the animals three hours after the treatment with Alendronate or Alendronate nitrate.

The results are reported in Table III and show that the administration of Alendronate nitrate reduces the level of the gastric damage from 4 to 5 times in comparison with the one noticed after the Alendronate supply.

TABLE I

| Treatment | Dose mg/Kg/p.o. | Gastric damage (% incidence) |
|---|---|---|
| Control | — | 0 |
| Piroxicam.HCl | 100 | 100 |
| Piroxicam.HNO$_3$ | 100 | 20 |

TABLE II

| Treatment | Myeloperoxydase activity (unit/mg tissue) |
|---|---|
| carrier | 111 ± 19 |
| 5-ASA | 72 ± 15 |
| 5-ASA-NO$_2$.HCl | 111 ± 20 |
| 5-ASA-NO$_2$.HNO$_3$ | 35 ± 13 |

TABLE III

| Treatment | Dose Alendronate mg/Kg/p.o. | Gastric damage (% incidence) |
|---|---|---|
| Alen. | 80 | 1.8 ± 2.2 |
| Alen. + Asp. | 80 | 36.2 ± 4.1 |
| Alen.HNO$_3$ + Asp. | 80 | 8.6 ± 1.6 |

What is claimed is:

1. A nitrate salt of a compound selected from the group consisting of:

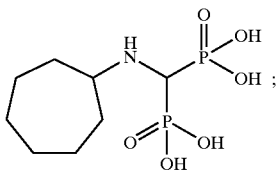
(F1e)

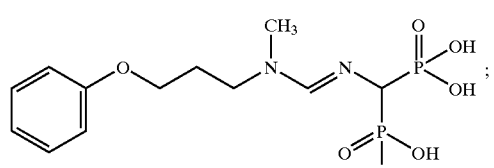
(F1f)

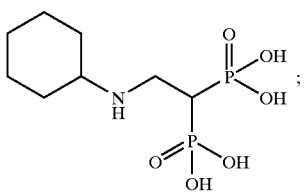
(F1h)

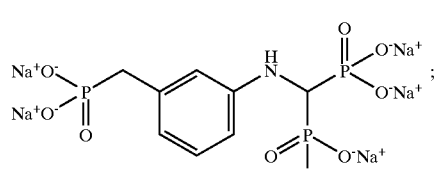
(F1o)

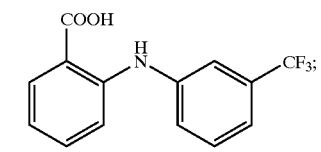
(F2AVII)

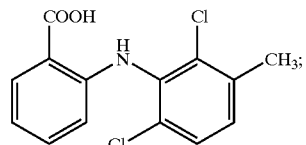
(F2AVIII)

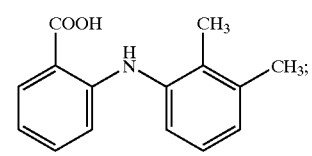
(F2AIX)

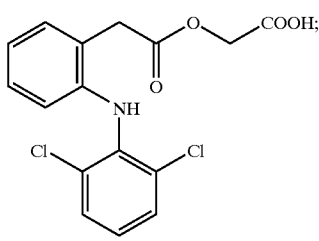
(F2AXI)

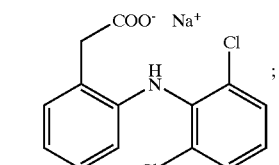
(F2AXII)

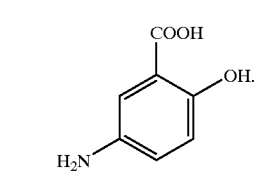
(F2AXIV)

2. A nitrate salt according to claim 1 wherein the compounds are selected from the group consisting of Diclofenac (F2AXII) and Flufenamic acid (F2VII).

3. A nitrate salt according to claim 1 wherein the compounds contain one or more —ONO$_2$ groups covalently bound to the molecule by one of the following bivalent linking bridges:

YO wherein Y is a C$_1$–C$_{20}$ alkylene linear or branched when possible, preferably from 2 to 5 carbon atoms, or a cycloalkylene from 5 to 7 carbon atoms;

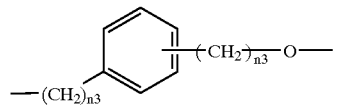

wherein n3 is an integer from 0 to 3;

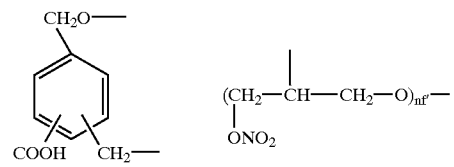

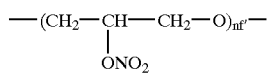

wherein nf is an integer from 1 to 6; and

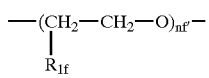

wherein $R_{1f}$=H, $CH_3$ and nf is an integer from 1 to 6.

4. A nitrate salt according to claim 3 wherein the compounds containing —$ONO_2$ groups covalently bound to the molecule by bivalent linking bridges are selected from the compounds of grouping F2A.

5. Nitrate salts according to claim 1, containing one or more isomers of said compounds.

6. Nitrate salts according to claim 1, wherein the salts of said compounds contain one nitrate ion/compound mole.

7. A pharmaceutical composition comprising a nitrate salt according to claim 1 and a pharmaceutically acceptable carrier.

8. A method of treating bony disorders in a patient in need of such treatment, wherein said method comprises administering a bony disorder treating effective amount of a medicament comprising at least one nitrate salt according to claim 1, or tramadol nitrate, to said patient.

9. A method of treating bony disorders in a patient in need of such treatment, wherein said method comprises administering a bony disorder treating effective amount of a medicament comprising at least one nitrate salt according to claim 1, or tramadol nitrate to said patient.

10. A process for preparing nitrate salts according to claim 1, wherein, when the substance to be salified is available as a base or as a corresponding salt soluble in an organic solvent, which does not contain hydroxyl groups, the salt is prepared by dissolving the substance in the solvent at a concentration equal or higher than 10%. w/v, adding the amount of concentrated nitric acid corresponding to the moles of salifiable aminic groups present in the compound, cooling during and after the addition at temperatures between 20° C. and 0° C. and recovering the product by filtration.

11. A process according to claim 10 wherein when the substance is not very soluble, or it is available as a not very soluble salt in the above mentioned solvents, the corresponding mixtures with hydroxylated solvents are used and precipitation is quickened by diluting the so obtained mixture, after the addition of nitric acid, with an apolar solvent.

12. A process according to claim 10 wherein when the starting product is salified with hydrochloric acid, the salt with nitric acid is prepared by directly adding silver nitrate to the compound solution, filtering the silver chloride, the solution is concentrated and cooled to recover the nitrate salt.

13. A process for preparing nitrate salts according to claim 1 wherein when the starting product is a salt, the corresponding base can be liberated by a treatment with a sodium or potassium bicarbonate or carbonate saturated solution, or with a sodium or potassium hydroxide diluted solution, extracting the base by a suitable organic solvent.

14. A process for preparing nitrate salts according to claim 13, wherein the substance to be salified is available as a base or as a corresponding salt soluble in an organic solvent, which does not contain hydroxyl groups, the salt is prepared by dissolving the substance in the solvent at a concentration equal or higher than 10% w/v, adding the amount of concentrated nitric acid corresponding to the moles of salifiable aminic groups present in the compound, cooling during and after the addition at temperatures between 20° C. and 0° C. and recovering the product by filtration.

15. A process for preparing nitrate salts according to claim 14, wherein when the substance is not very soluble, or it is available as a not very soluble salt in the above mentioned solvents, the corresponding mixtures with hydroxylated solvents are used and precipitation is quickened by diluting the so obtained mixture, after the addition of nitric acid, with an apolar solvent.

16. The nitrate salt of claim 3, wherein nf is an integer from 2 to 4.

17. The nitrate salt of claim 3, wherein nf is an integer from 2 to 4.

* * * * *